(12) United States Patent
Draudt et al.

(10) Patent No.: US 8,357,107 B2
(45) Date of Patent: Jan. 22, 2013

(54) BLOOD GLUCOSE METER HAVING INTEGRAL LANCET DEVICE AND TEST STRIP STORAGE VIAL FOR SINGLE HANDED USE AND METHODS FOR USING SAME

(75) Inventors: Gregg R. Draudt, Stow, MA (US); Dirk Ahlgrim, Boston, MA (US); Jan Schminke, München (DE); Mark Follman, Glen Rock, NJ (US); José Colucci, Jr., Lexington, MA (US); Raymond Yao, Saint Joseph, MI (US); Robert J. McCaffrey, Hillsboro, NH (US); Victor Chan, Landing, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 517 days.

(21) Appl. No.: 11/980,651

(22) Filed: Oct. 31, 2007

(65) Prior Publication Data

US 2008/0058631 A1 Mar. 6, 2008

Related U.S. Application Data

(63) Continuation of application No. 11/106,728, filed on Apr. 15, 2005, now abandoned.

(60) Provisional application No. 60/562,536, filed on Apr. 16, 2004.

(51) Int. Cl.
*A61B 5/00* (2006.01)
*B65D 81/00* (2006.01)

(52) U.S. Cl. ........................................................ 600/584

(58) Field of Classification Search .................. 600/573, 600/583, 584; 606/181–183; 221/232; 422/56; 436/60, 128
See application file for complete search history.

(56) References Cited

U.S. PATENT DOCUMENTS

| | | | |
|---|---|---|---|
| 4,787,398 A | 11/1988 | Garcia et al. |
| 5,279,294 A | 1/1994 | Anderson et al. |
| D418,602 S | 1/2000 | Prokop et al. |
| D425,990 S | 5/2000 | Gravel et al. |
| D427,312 S | 6/2000 | Douglas |
| 6,093,156 A | 7/2000 | Cunningham et al. |
| D429,527 S | 8/2000 | Bolam et al. |
| D429,814 S | 8/2000 | Lorwald et al. |
| 6,099,484 A | 8/2000 | Douglas et al. |
| D435,657 S | 12/2000 | Bhullar et al. |

(Continued)

FOREIGN PATENT DOCUMENTS

DE 42 34 553 A1 4/1993

(Continued)

*Primary Examiner* — Brian Szmal
(74) *Attorney, Agent, or Firm* — Roylance, Abrams, Berdo and Goodman, LLP

(57) ABSTRACT

A blood glucose meter having a test strip port and an adjustable lancet device disposed at the same end of the device body is disclosed. The device body further includes an enclosure at the proximal end of the device body which houses a test strip storage vial and which facilitates one-handed opening and closing of the vial to simplify access to test strips contained therein. The enclosure is further provided with a window which allows the reading of the lot numbers on the label of the test strip vial therein without necessitating removal of the vial. A data connector is also provided on the device body for communication access, such as to upload data from other devices or to download data to other devices. By combining these multiple components into a single device body, the blood glucose meter requires fewer steps for sampling and testing, and makes device use easier and more convenient.

8 Claims, 16 Drawing Sheets

U.S. PATENT DOCUMENTS

| | | |
|---|---|---|
| D448,294 S | 9/2001 | Alscher et al. |
| 6,302,855 B1 | 10/2001 | Lav et al. |
| 6,352,514 B1 | 3/2002 | Douglas et al. |
| D471,280 S | 3/2003 | Jaeck |
| 6,620,112 B2 | 9/2003 | Klitmose |
| 6,645,219 B2 | 11/2003 | Roe |
| D487,594 S | 3/2004 | Alscher et al. |
| D491,275 S | 6/2004 | Walters et al. |
| D493,536 S | 7/2004 | Jaeck et al. |
| D506,007 S | 6/2005 | Best et al. |
| 6,994,261 B2 | 2/2006 | Eilersen |
| 7,001,344 B2 | 2/2006 | Freeman et al. |
| 7,192,405 B2 | 3/2007 | De Nuzzio et al. |
| 2001/0027277 A1 | 10/2001 | Klitmose |
| 2002/0130042 A1 | 9/2002 | Moerman et al. |
| 2002/0177763 A1 | 11/2002 | Burns et al. |
| 2003/0191415 A1 | 10/2003 | Moerman et al. |
| 2003/0212345 A1 | 11/2003 | McAllister et al. |
| 2003/0223905 A1 | 12/2003 | Moerman |
| 2004/0007585 A1 | 1/2004 | Griffith et al. |
| 2004/0138588 A1 | 7/2004 | Saikley et al. |
| 2004/0267229 A1 | 12/2004 | Moerman et al. |
| 2005/0011759 A1 | 1/2005 | Moerman et al. |
| 2005/0143675 A1 | 6/2005 | Neel et al. |
| 2005/0177072 A1 | 8/2005 | Kloepfer et al. |
| 2005/0240119 A1 | 10/2005 | Draudt et al. |

FOREIGN PATENT DOCUMENTS

| | | |
|---|---|---|
| EP | 1 321 769 A1 | 6/2003 |
| EP | 1 362 551 A1 | 11/2003 |
| GB | 2 374 019 A | 10/2002 |
| WO | WO 03/015627 A2 | 2/2003 |
| WO | WO 03/015627 A3 | 2/2003 |
| WO | WO 03/082091 A2 | 10/2003 |
| WO | WO 03/082091 A3 | 10/2003 |
| WO | WO 2005/102154 A2 | 11/2005 |
| WO | WO 2005/102154 A3 | 11/2005 |

BLOOD GLUCOSE METER HAVING INTEGRAL LANCET DEVICE AND TEST STRIP STORAGE VIAL FOR SINGLE HANDED USE AND METHODS FOR USING SAME

CROSS-REFERENCE TO RELATED APPLICATIONS

This is a continuation application of application Ser. No. 11/106,728, filed Apr. 15, 2005 now abandoned, which claims priority under 35 U.S.C. §119(e) from a U.S. Provisional Patent Application of Gregg Draudt et al., entitled "Blood Glucose Meter Having Integral Lancet And Vial Storage For Single Handed Use And Method For Using Same", Ser. No. 60/562,536, filed on Apr. 16, 2004, the entire contents of which are incorporated herein by reference.

FIELD OF THE INVENTION

The present invention relates to a blood glucose meter with an integral lancet device, and a location on the device to store test strip vials, such that one-handed use for lancet device, meter and test strip access functions are possible.

BACKGROUND OF THE INVENTION

As the number of patients suffering from diabetes and similar medical conditions increases, self-monitoring of blood glucose wherein the patient monitors his or her blood glucose levels has become a common practice. Various mechanisms have been created to achieve these results, and typically include a lancet device and a blood glucose meter.

Blood glucose meters often further include a memory for storing measured blood glucose values, exercises and meals, along with other related data such as the corresponding dates, time of day, and duration of each, and the units that were used as these values and events were measured. Blood glucose meters are also generally provided with a display screen and user input buttons or controls with which a user can specify which of the stored values to display or functions to access.

A blood glucose meter can be configured to receive and read an inserted test strip on which a drop of a patient's blood has been deposited. Still other devices include an integrated lancet device and glucose meter for ease of self-monitoring. Such systems are disclosed, for example, in U.S. Pat. No. 4,787,398, to Garcia et al., entitled "Glucose Medical Monitoring System", the entire content of which is incorporated herein by reference.

In many devices, the lancet mechanism and the detection mechanism are separate. In doing so, the lancet device including the lancet, and the detection unit including the test strip, which are provided separately or are separately mounted on a monitoring system, result in a very complicated operation for the user.

Accordingly, a need exists for a device and method to provide a blood glucose meter with an integral lancet device, and a location on the device to store test strip vials, such that one-handed use for lancet device, meter and test strip access functions are possible.

SUMMARY OF THE INVENTION

It is therefore an object of the present invention to provide a blood glucose meter with an integral lancet device, and a location on the device to store a test strip vial, such that one-handed use for lancet device, meter and test strip access functions are possible.

It is another object of the present invention to provide a blood glucose meter with an integral lancet device such that lancing and testing processes are positioned sufficiently close in proximity to allow a virtually continuous short motion by the user to achieve the functions of each.

It is another object of the present invention to provide a blood glucose meter with a location on the device to store test strip vials, such that vial access can be achieved using a one-handed motion.

It is another object of the present invention to provide a blood glucose meter with a location on the device to store test strip vials, such that vial content information is visible to a user without removal of the vial from the device.

It is another object of the present invention to provide a blood glucose meter providing further analytical functions, including communication with other devices.

These and other objects are substantially achieved by providing a blood glucose meter having a test strip port and adjustable lancet device disposed at the same end of the device body. The device further includes an enclosure at an opposite end which houses a test strip vial, and which further facilitates one-handed opening and closing of the vial to simplify access to the contained test strips. A data connector or wireless communication module can be located on the bottom of the enclosure of the device for communication access, such as to upload data from other devices and download data to other devices, and a window can be provided on a device surface which allows the reading of lot numbers on the label of the test strip vial without requiring the removal of the vial from the device.

BRIEF DESCRIPTION OF THE DRAWINGS

The above and other objects and advantages will become more apparent upon consideration of the following drawings and detailed description, in which.

DETAILED DESCRIPTION OF THE EXEMPLARY EMBODIMENTS

The exemplary embodiments of the present invention described below relate to a blood glucose meter with an integral lancet device, and a location on the device to store a test strip vial that holds a number of test strips. The disclosed embodiments of the present invention combine the functionality of each above feature into a streamlined enclosure that optimizes the use of the product for the purpose of monitoring one's blood glucose.

Figure 1:
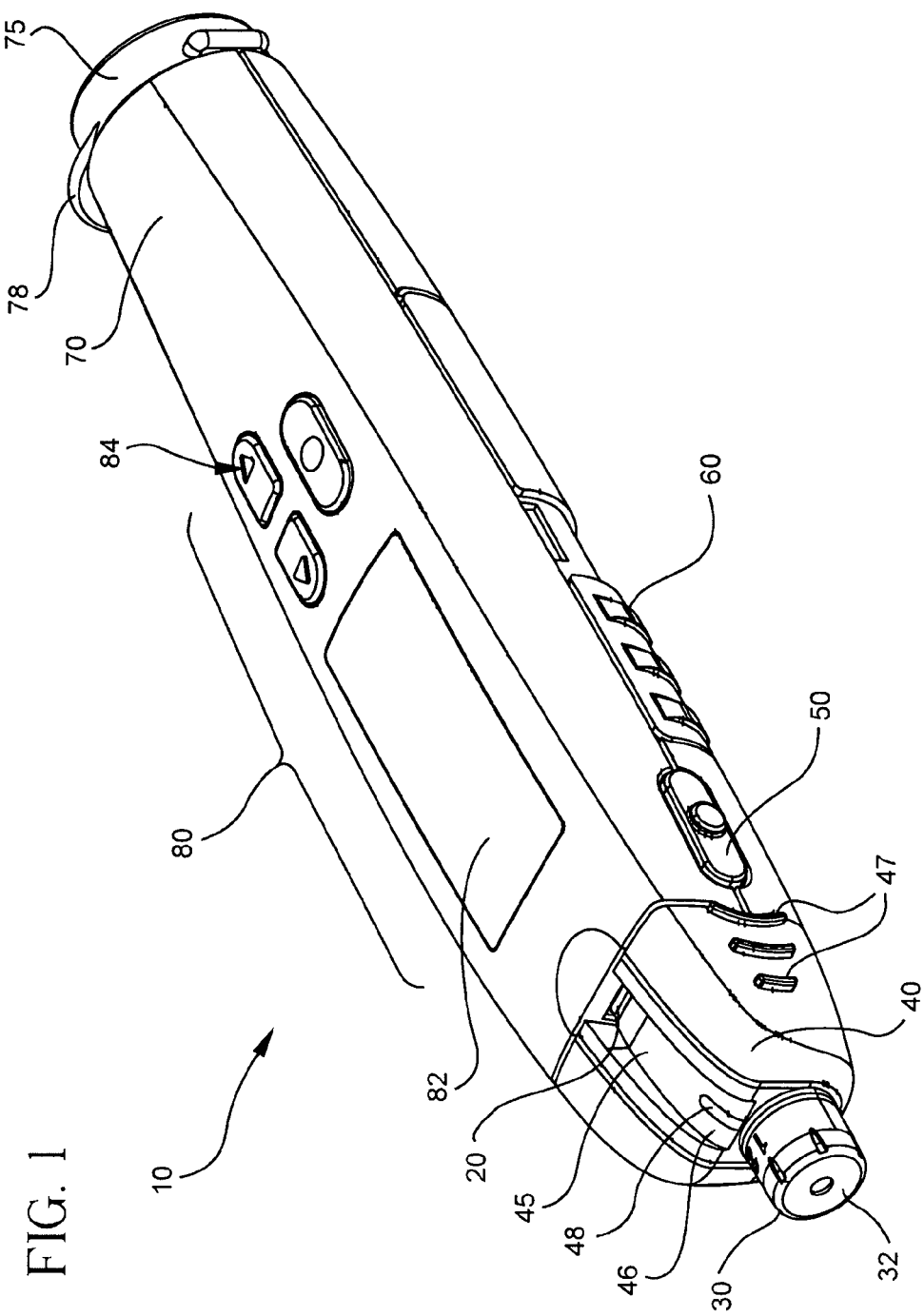
FIG. 1 is a perspective view illustrating the top surface of a blood glucose meter in accordance with an embodiment of the present invention.

FIG. 1 is a perspective view illustrating the top surface of a blood glucose meter in accordance with an embodiment of the present invention. The main features of the disclosed embodiments of the present invention include a device body 10 configured for convenient one-handed use, test strip port 20 and lancet device 30 that are disposed at the same end of the device body 10, thereby allowing a drop of blood extracted by the lancet device 30 to be immediately deposited on the test strip (not shown) in the test strip port 20, a detachable cover 40 which allows lancet replacement and also provides a generous lead-in area 45 to facilitate convenient test strip loading into the test strip port 20, a trigger button 50 on the side of the device body 10 which allows comfortable positioning during lancing, an arming slide 60 on the sides and bottom of the enclosure of the device body 10 which arms the lancing mechanism of the lancet device 30 when moved toward the back of the device, wherein the location of the arming slide 60 keeps the outer size of device body 10 as small as possible, and an enclosure 70 which houses a test strip vial 75 containing multiple test strips and which allows one-handed vial opening. The device body 10 further includes a blood glucose meter 80 for processing the test strip, and a data connector 90 (see FIG. 2) located on the bottom of enclosure for data exchanges with an electronic pen-type injector or other device. The blood glucose meter 80 can further include a display window 82 and a plurality of meter operation buttons or controls 84. The enclosure 70 can further include a window 72 which allows reading of a test strip lot number on a test strip vial 75 label therein without removing the strip vial from the device body 10. By combining these multiple components into a single device body 10, the device requires fewer steps for testing, and makes device use easier, even in confined or less than ideal locations to test one's blood glucose levels.

As noted above, many existing devices require the use of a separate blood glucose meter, lancet device and test strip storage vial. These existing devices can, therefore, require an extensive amount of handling and manipulation of separate devices to facilitate the measurement of one's blood glucose, which is an undesirable outcome. The exemplary embodiments of the present invention combine these separate device features into a single device by combining a blood glucose meter, lancet device and test strip storage, thereby requiring much less handling and manipulation to accomplish a desirable outcome.

The embodiment of the present invention shown in FIG. 1 takes advantage of the small size of the primary sub-components, including blood glucose sensing circuitry/technology of the blood glucose meter 80, lancet mechanism of the lancet device 30, and test strip storage vial 75, and encapsulates each in an attractive and user-friendly package. The combination of these sub-systems as shown in the embodiment of FIG. 1 results in a reduction in the number of steps required to test one's blood glucose as described in greater detail below. The blood glucose sensing circuitry/technology of the blood glucose meter 80, lancet mechanism of the lancet device 30, and test strip storage vial 75 are well known to those skilled in the art and a detailed description of each is omitted for clarity and conciseness.

Figure 2:
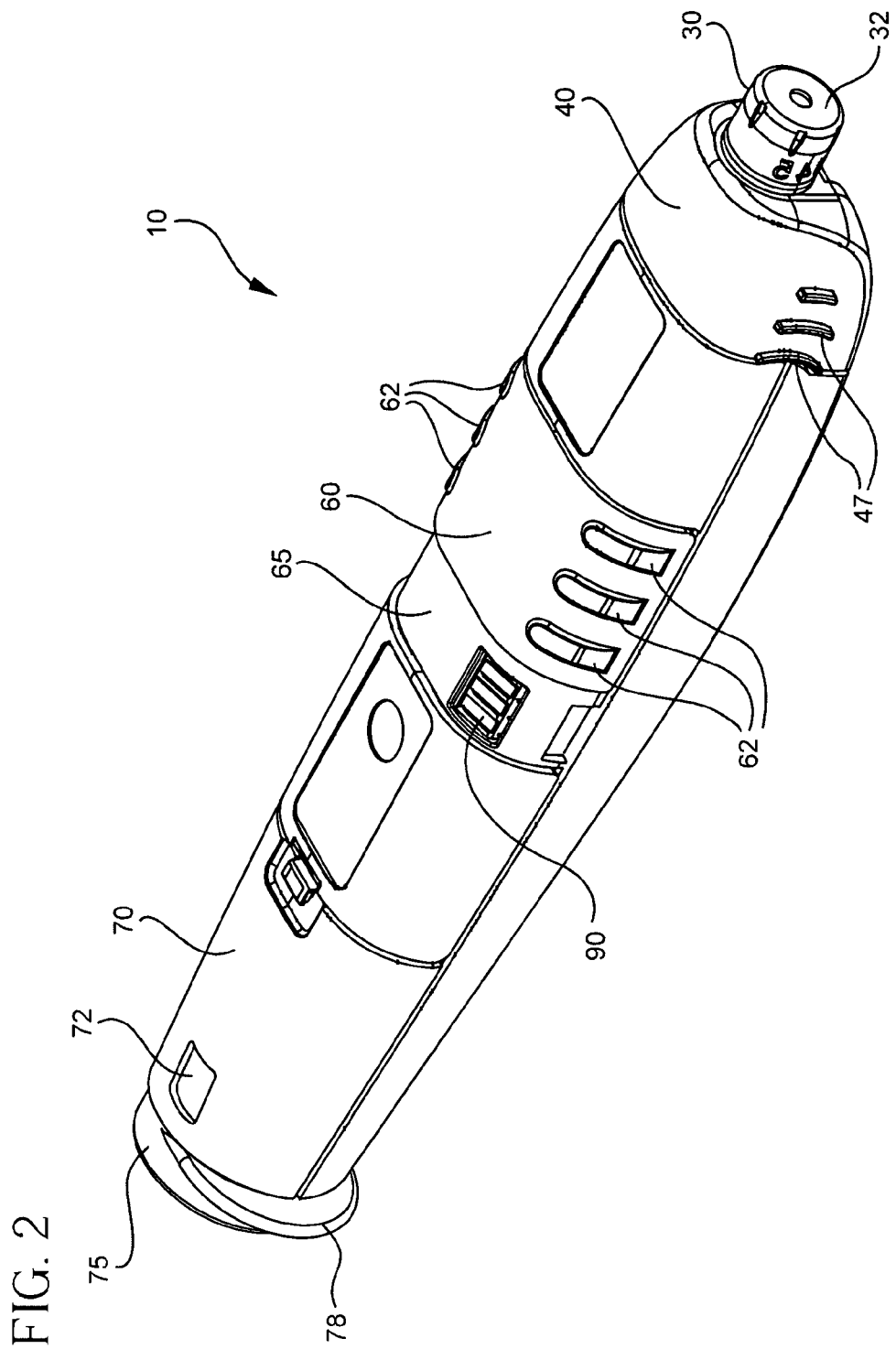
FIG. 2 is a perspective view illustrating the bottom surface of the embodiment of FIG. 1.

FIGS. 1 and 2 illustrate a first embodiment of the present invention. FIG. 1 is a perspective view illustrating the top surface of the device, and FIG. 2 is a perspective view illustrating the bottom surface of the device.

The device of FIG. 1 includes a device body 10 which is configured for convenient one-handed use. The device body 10 comprises a tapered cylindrical housing having flattened top and bottom surfaces. The device body 10 can be any suitable length, but preferably comprises a length of about 160 mm. The top and bottom surfaces of the device body 10 preferably have a width of about 25 mm. The device body 10 can be constructed of any suitable material, but is preferably constructed of an engineering plastic material.

At a distal end of the device of FIG. 1, a test strip port 20 and adjustable lancet device 30 are disposed at the same end of the device body 10. In doing so, a test strip (not shown) can be provided very close to the lancet device 30. A generous lead-in area 45 is provided to the test strip port 20 for improved usability, and can comprise a color highlighted area surrounding the opening of the test strip port 20 to provide improved visibility. The lead-in area 45 can be provided for holding the test strip during use, and can be constructed as a notch at the distal end of the device body 10 extending from an open end 46 at the distal end of the device to the test strip port 20, and having a slightly wider opening at the open end 46 of about 7.0 mm, which narrows to equal the opening of the test strip port 20. The lead-in area 45 can be provided having any suitable length, but is preferably about 18 mm long. The test strip port 20 can be provided to be within 27.6 mm of the distal end of the lancet device 30. Accordingly, a test strip when positioned in the lead-in area 45 can be provided to be within 3.8 mm of the distal end of the lancet device 30.

A detachable cover 40 is provided and allows convenient lancet replacement when desired. Contours and/or recesses in the detachable cover 40 can provide the lead-in area 45 to guide the test strip into the test strip port 20. The detachable cover 40 can be constructed of any suitable material, but is preferably constructed of the same material as the device body 10. The detachable cover 40 can be secured to the device body 10 using any number of attachment mechanisms, such as a snap-fit mechanism. Grip features 47 comprising a number of raised ribs are provided on the sides of the detachable cover 40 to aid in the removal and replacement of the cover 40 from and to the device body 10.

A trigger button 50 is disposed on one or both sides of the device body 10, allowing comfortable positioning during lancing when using either a right or left hand. The trigger button 50 is mechanically engaged with the lancet mechanism of the lancet device 30 through the device body 10 to activate the lancet as known to those skilled in the art when a force is exerted on the trigger button 50, such as when pressed by a user. An arming slide 60 is disposed on the sides and bottom of the device body 10 to minimize the overall envelope of the device. The arming slide 60 is also mechanically engaged with the lancet mechanism of the lancet device 30 through the device body 10 to arm the lancet as known to those skilled in the art through a sliding motion of the arming slide 60, such as when slid by a user. Accordingly, the arming slide 60 can be disposed within a recess 65 extending over the sides and bottom of the device body 10. The arming slide 60 can be guided in the recess 65 using any number of mechanisms, such as rails (not shown) disposed along each side of the recess 65 and engaged by the arming slide 60. By further providing the arming slide 60 with a number of raised members 62, a user can firmly grasp the arming slide 60 with one hand and arm the lancet by pressing the proximal end of the device body 10 against a surface to move the arming slide 60 within the recess 65.

The device further includes an enclosure 70 in the proximal end of the device body 10 which houses a test strip vial 75, and which facilitates one-handed opening and closing of the test strip vial 75 to simplify access to test strips contained therein. The enclosure 70 can be an axial opening in the device body 10, having a sufficient diameter and which extends to a sufficient depth to receive a test strip vial 75. In an exemplary embodiment of the present invention, the enclosure 70 can have an opening of 18 mm and a depth of 35.4 mm. The enclosure 70 can further comprise a retention feature for the test strip vial 75, such as a friction-type retention feature or a positive mechanical lock, for engaging and retaining the test strip vial 75 therein. The extended cap or lid 78 of the test strip vial 75 remains exposed and extending from the proximal end of the device body 10, which allows one-handed opening of the test strip vial 75 as described in greater detail below.

The enclosure 70 further comprises a window 72 which allows the reading of the lot numbers on the label of the test strip vial 75 therein without necessitating the removal of the test strip vial 75 from the enclosure 70. The window 72 can be constructed of any suitable clear material, and can be further provided with a lens to enlarge the text of the test strip vial 75 label.

The device body 10 further includes a lancet device 30 for lancing a skin surface and providing a blood sample to a test strip (not shown) held in the lead-in area 45. The tip of the lancet device 30 comprises a substantially cylindrical depth control mechanism 32 against which the user engages a skin surface. Accordingly, the lancet device 30 can be adjustable. In the embodiments of the present invention, the depth setting is selected by rotating the cylindrical depth control mechanism 32 to the desired setting number positioned adjacent to the depth selection indicator 48. Further, the lancet device 30 can be armed and activated as described above, and can include a lancet (not shown) that can be easily accessed via the detachable cover 40.

The device body 10 further includes a blood glucose meter 80 for processing the test strip (not shown) received via the test strip port 20. The blood glucose meter 80 can further include a display window 82, such as an LCD display or like device, which can display any number of test results. A plurality of blood glucose meter operation buttons or controls 84 can be provided to allow a user to control the meter 80 and meter display window 82. A data connector 90 can be provided with the blood glucose meter 80 for communication access, such as to upload data from other devices or to download data from the device to other devices. The data connector 90 can be disposed on the bottom of device body 10 for data exchanges with an electronic pen-type injector or other devices, and can comprise any number of hardwired or wireless communication connectors. Preferably, the data connector 90 comprises a multiple contact electrical connector, such as a three contact electrical connector.

The use of the disclosed embodiments of the present invention, described in greater detail below, significantly benefits from the combined features described above and shown in FIGS. 1 and 2. As noted above, the embodiments of the present invention include a blood glucose meter 80 with an integral lancet device 30, and a location 70 on the device body 10 to store a test strip vial 75 that holds a number of test strips (i.e., up to 25 or more). The embodiments further include the test strip port 20 for the glucose test strip, and the tip of the lancet of the integral lancet device 30, at the same end of the device body 10. In doing so, the embodiments of the present invention allow a user to insert a test strip into the lead-in area 45, arm the lancet device 30, lance a finger, and collect the blood on the edge of the test strip held in the lead-in area 45 with minimal wasted movement and time (i.e., a virtually continuous short motion). Such steps are outlined and illustrated in FIGS. 3 through 12.

Many existing devices provide the lancet device at the opposite end from the test strip, requiring the user to perform an awkward maneuver to rotate the unit after lancing. Still other existing devices require either the use of a separate lancet device in the case of meter-only units, or a rotation of the meter in the case of meters with lancet device and test strip port at opposite ends. The embodiments of the present invention solve these problems by placing the test strip port 20 and the lancet of the lancet device 30 in as close proximity as is ergonomically possible at the distal end of the device body 10, thereby minimizing wasted motion.

In the disclosed embodiments of the present invention, the geometry of the distal end or tip of the device, which includes the test strip port 20 and the lancet device 30 positioned close together, results from the use of a compact mechanism for the lancet device 30, and a compact integrated printed circuit board for the glucose meter 80 electronics. The device further provides the detachable cover 40 at the distal end, which provides a generous sized lead-in area 45 to guide the test strip into the test strip port 20. As noted above, the lead-in area 45 can further include a color highlighted area (not shown) surrounding the opening of the test strip port 20 for improved visibility and ergonomics.

Figure 3:
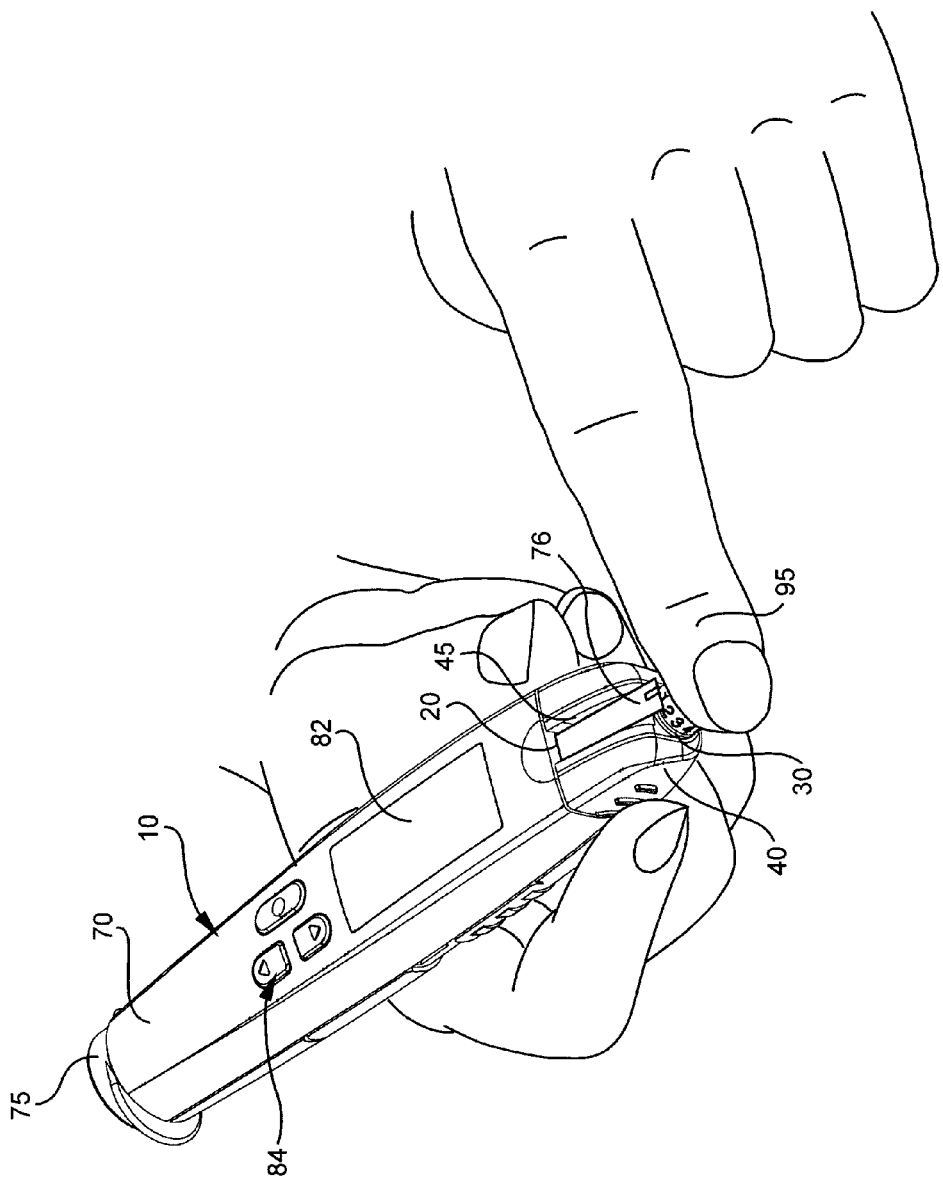
FIGS. 3 through 5 are views illustrating an exemplary manner of use of an embodiment of the present invention for lancing a finger to provide a blood drop.
Figure 4:
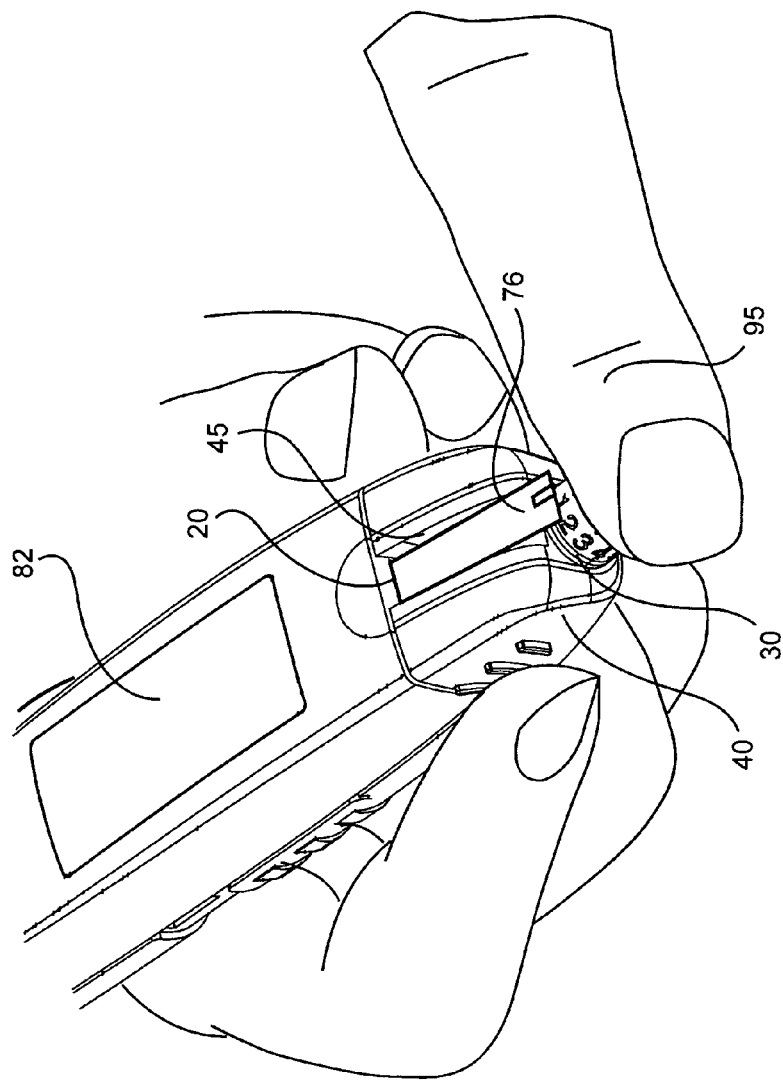
Figure 5:
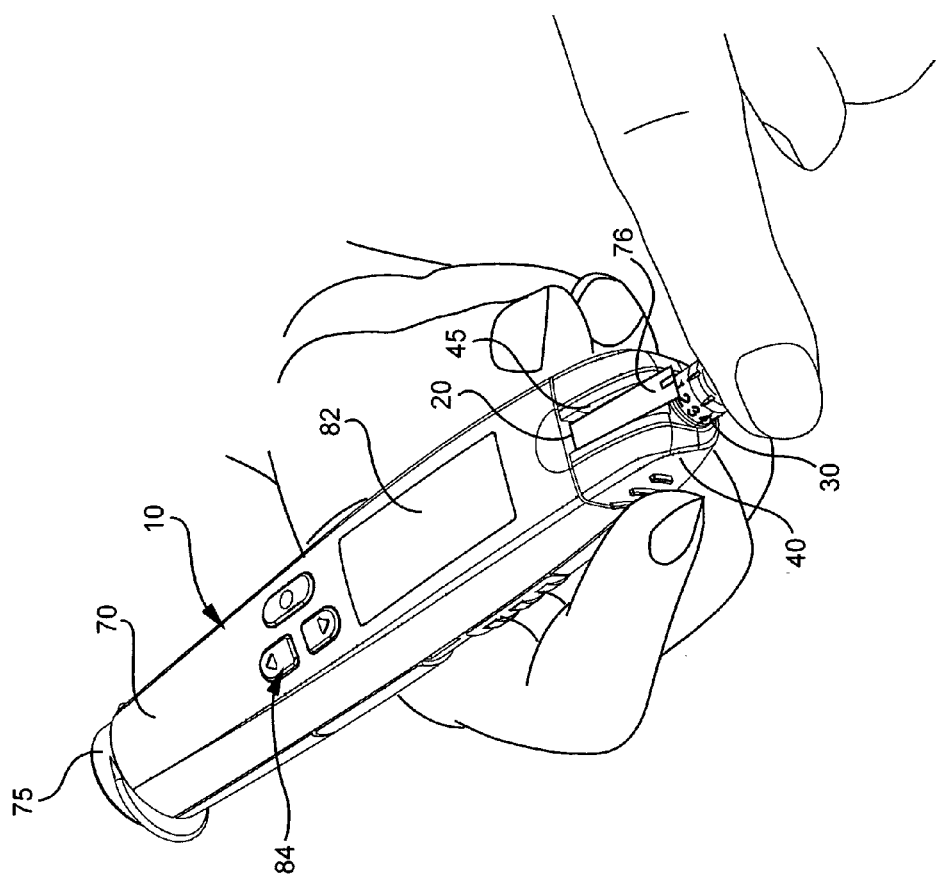
Figure 6:
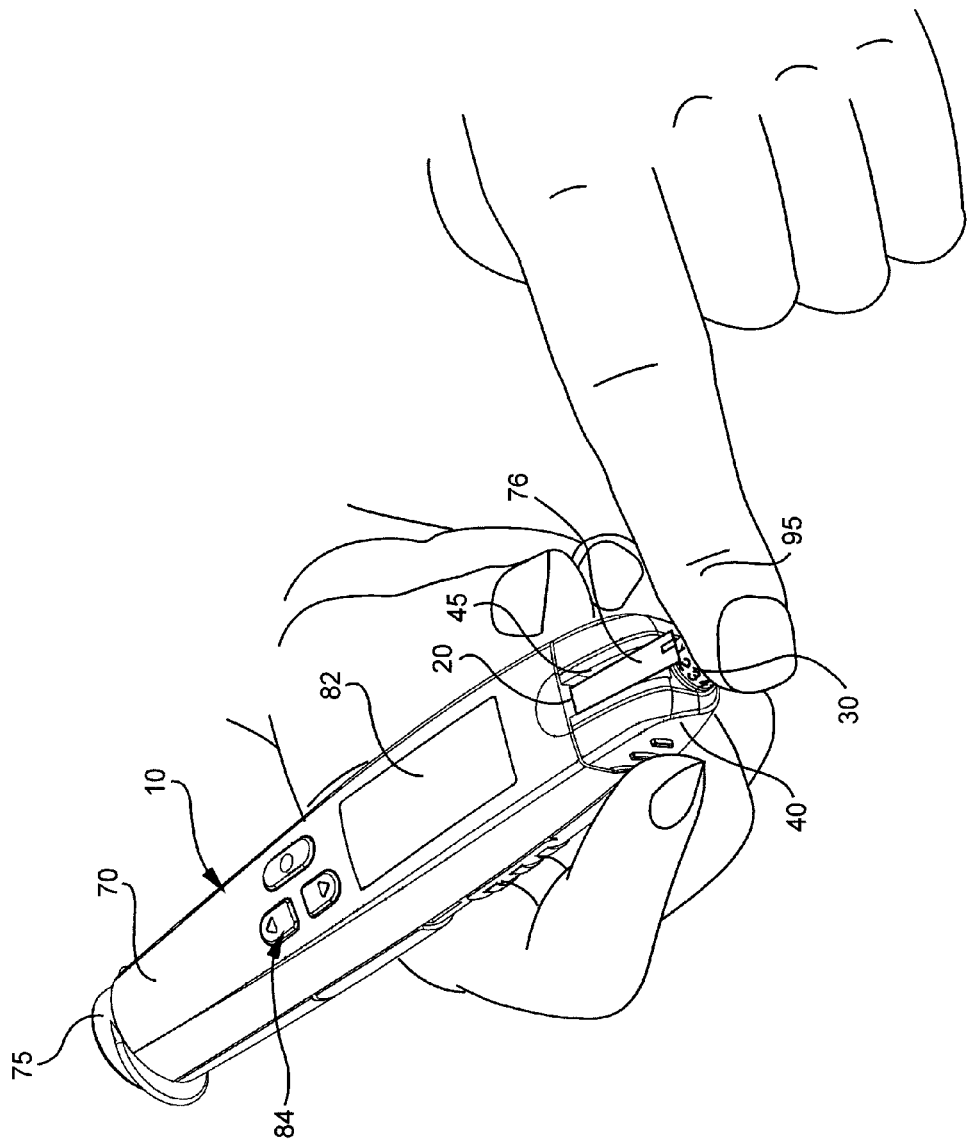
FIGS. 6 and 7 are views illustrating an exemplary manner of use of an embodiment of the present invention by rolling a bottom-lanced finger over a test strip using the stationary device end as a rest for the lanced finger to provide the blood drop to the test strip.
Figure 7:
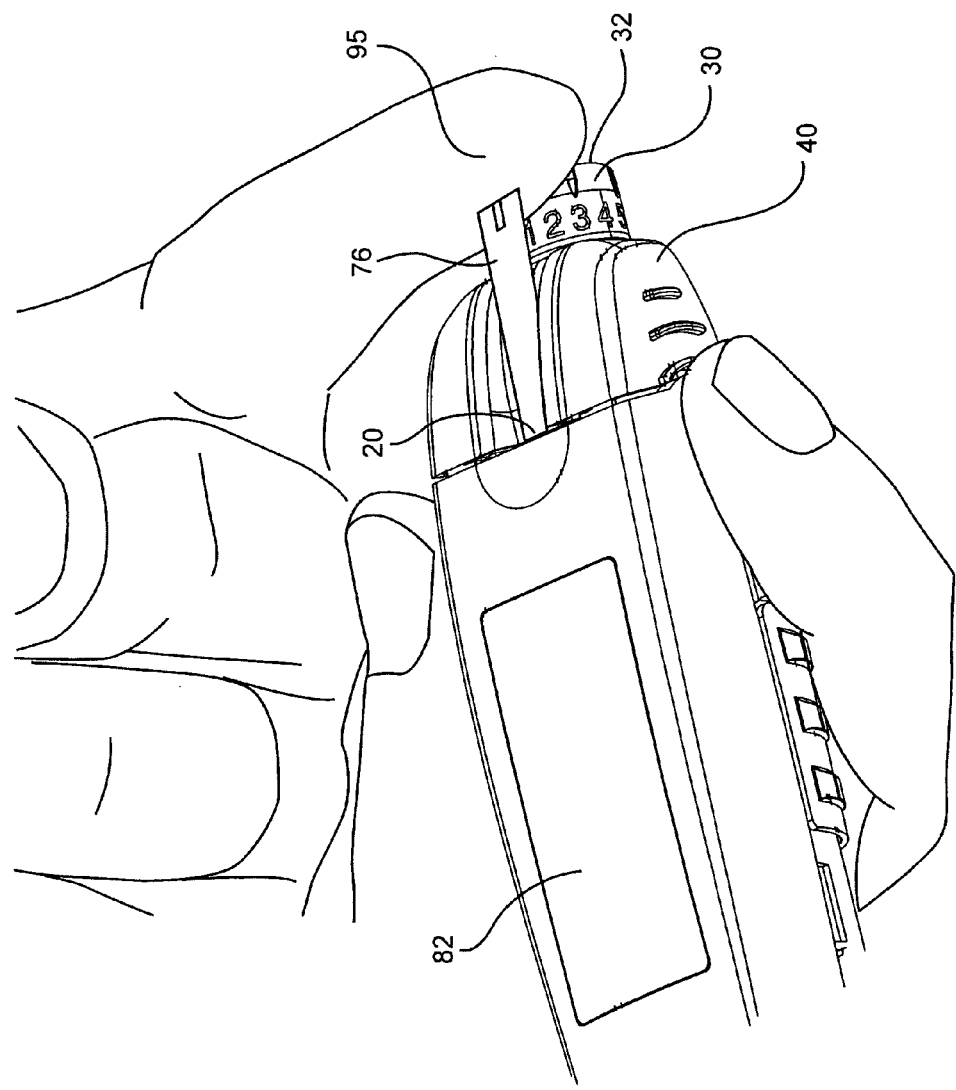
Figure 8:
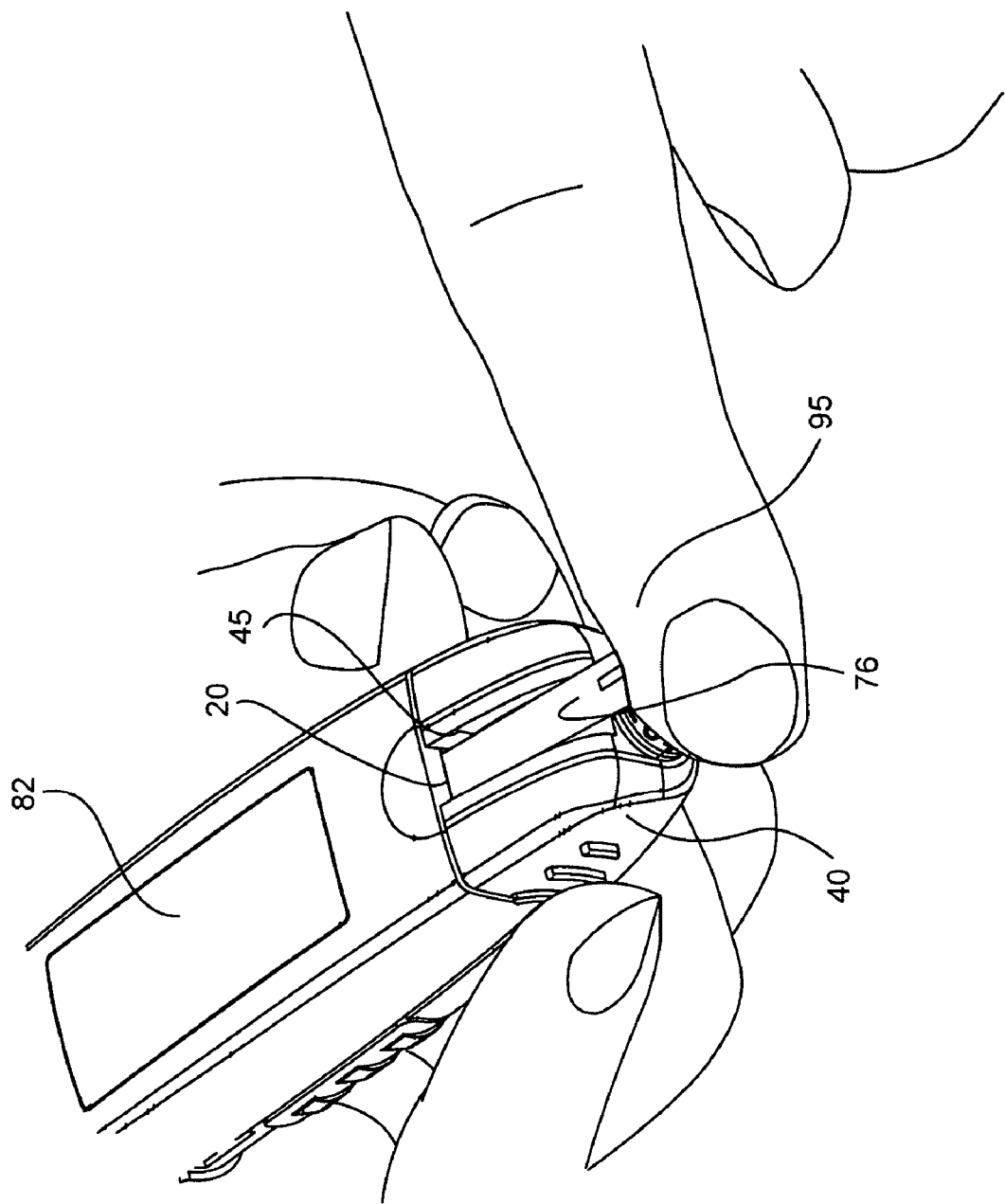
FIGS. 8 and 9 are views illustrating an exemplary manner of use of an embodiment of the present invention by moving a side-lanced finger a short distance to the test strip to provide the blood drop to the test strip.
Figure 9:
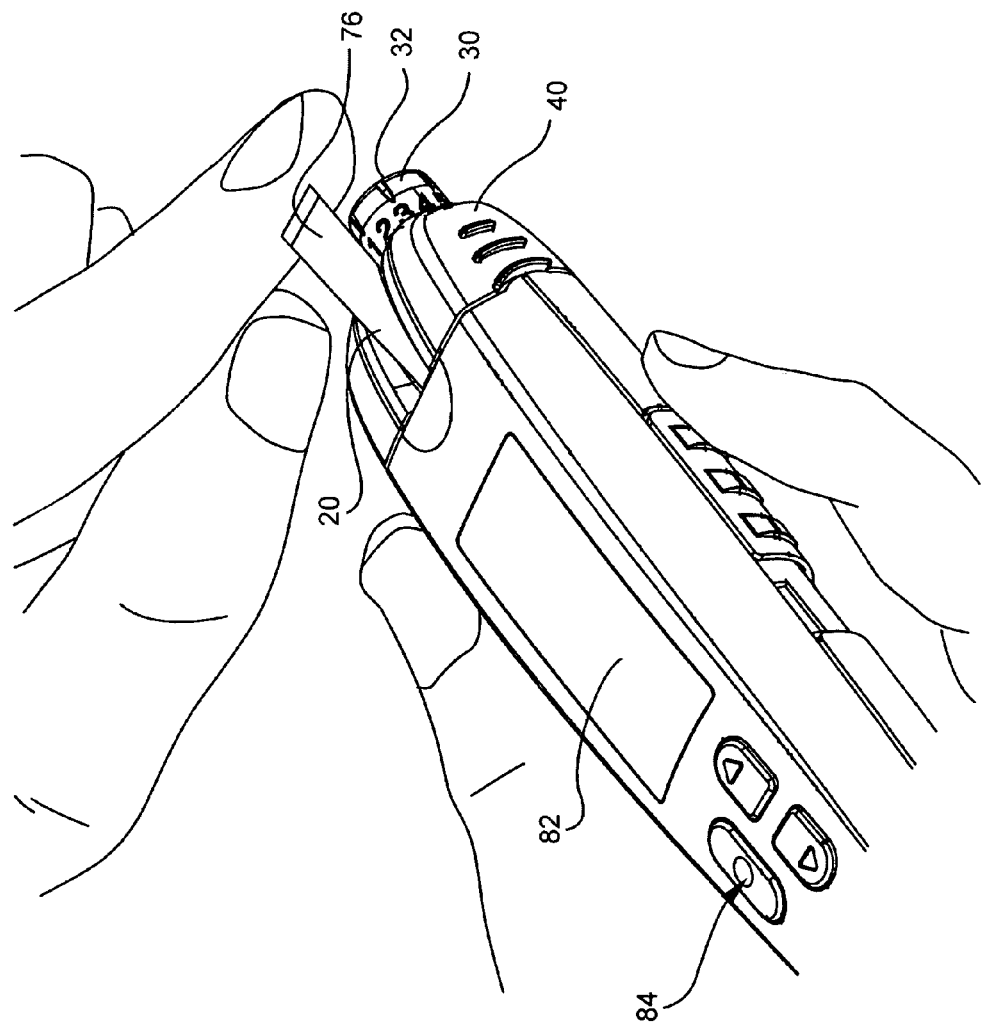

In the use of the embodiments of the present invention as illustrated in FIGS. 3 through 5, a tester can lance any number of positions on a skin surface, such as a bottom surface of a finger or a side surface of a finger. Specifically, FIG. 3 illustrates a lancing technique on a bottom surface of a finger, FIG. 4 illustrates a close-up view of the lancing technique of FIG. 3, and FIG. 5 is a view of a lancing technique on a side surface of a finger. Further, as illustrated in FIGS. 6 and 7, many testers after lancing a skin surface will prefer to use the tip of the device to support the lanced finger and gently roll it over the device tip to apply the blood drop onto the test strip held in the lead-in area 45. Specifically, FIG. 6 illustrates a bottom-lanced finger resting on the device tip, and FIG. 7 illustrates the bottom-lanced finger of FIG. 6 being rolled toward the test strip to apply the blood drop onto the test strip while resting on the device tip. However, as illustrated in FIGS. 8 and 9, many testers after lancing a skin surface may not desire to use the tip of the device to support the lanced finger, but prefer to simply move the lanced skin surface from the device tip to apply the blood drop onto the adjacent test strip held in the lead-in area 45. Specifically, FIG. 8 illustrates a side-lanced finger moved the short distance from the device tip to the test strip, and FIG. 9 illustrates the side-lanced finger of FIG. 8 being used to apply the blood drop onto the test strip.

Figure 10:
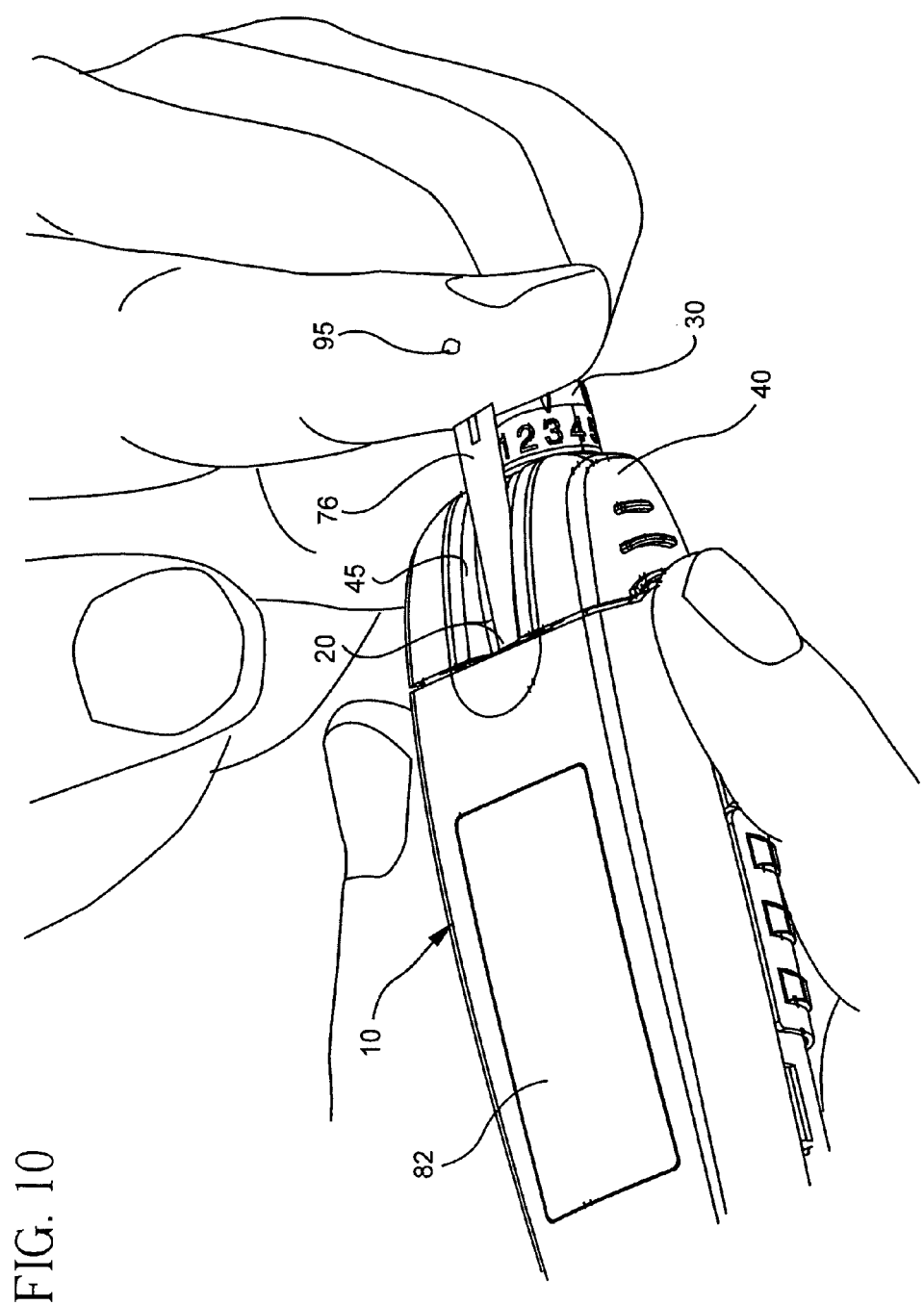
FIGS. 10 through 12 are views illustrating an exemplary manner of use of an embodiment of the present invention by rolling the finger over a stationary device to provide the blood drop to the test strip.
Figure 11:
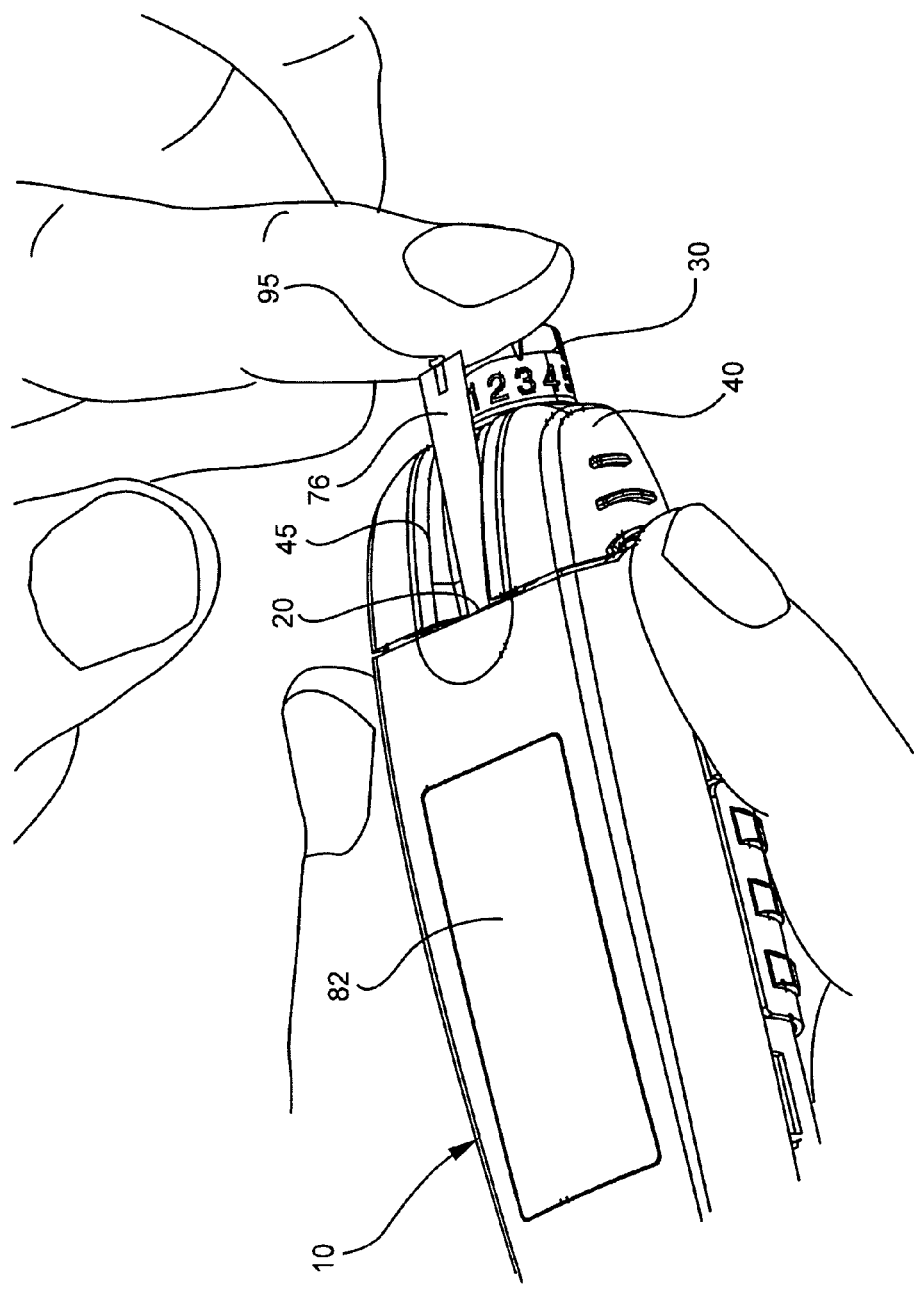
Figure 12:
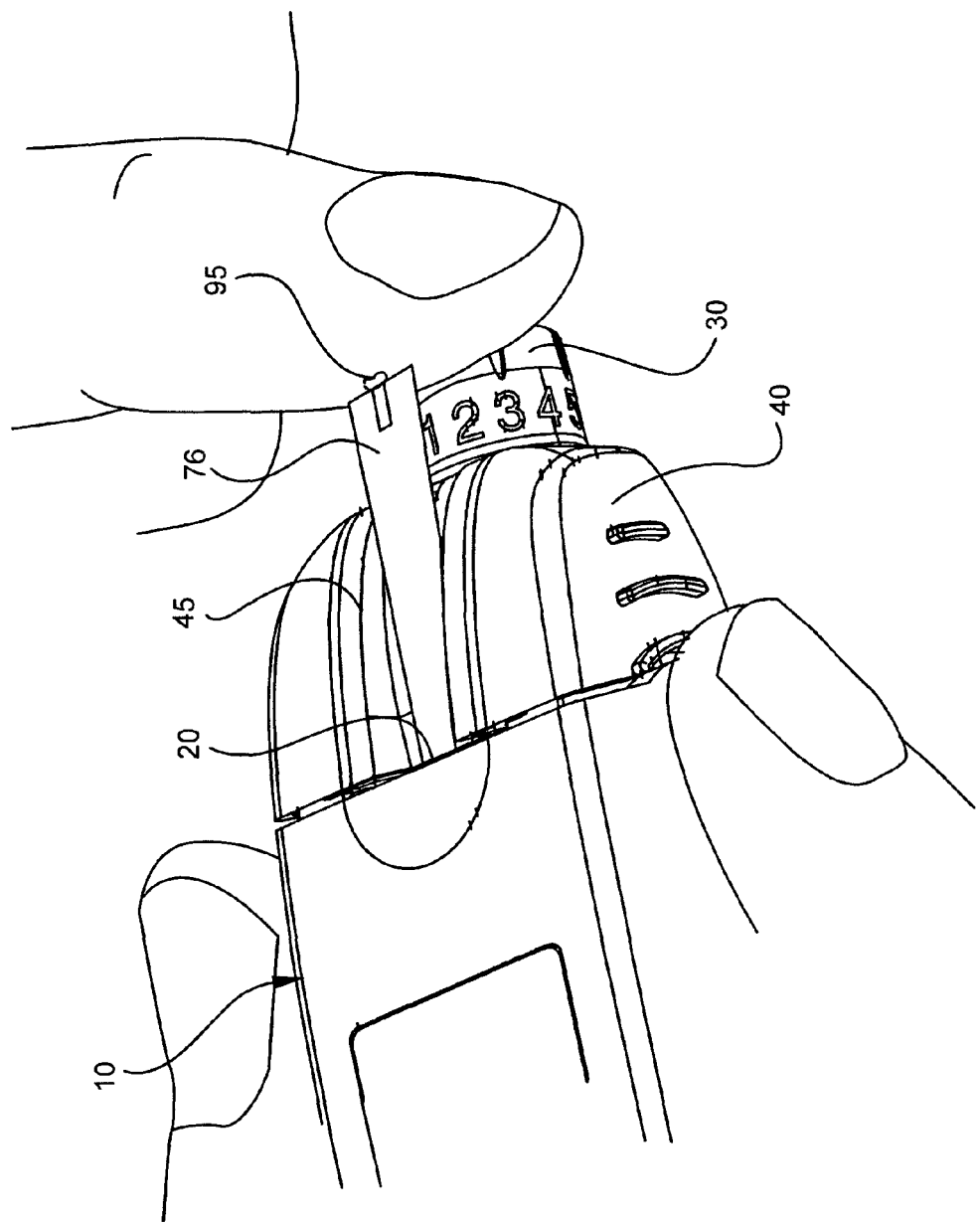

Still other testers may prefer to hold the device stationary and rotate the skin surface across the tip of the lancet device and to the adjacent test strip in a substantially continuous motion. As described below, such a "strip-to-tip rotate" method of use is shown in FIGS. 10 through 12. Still other testers after lancing a skin surface, may prefer to use a second or adjacent finger to support the lanced finger to gently roll it over and toward the test strip to apply the blood drop onto the test strip held in the lead-in area 45.

FIGS. 3 through 5 are views illustrating an exemplary manner of use of an embodiment of the present invention for lancing a finger after arming the device. As noted above, the user can first arm the lancet device 30 by firmly grasping the arming slide 60 with one hand and pressing the proximal end of the device body 10 against a surface to move the arming slide 60 within the recess 65.

In FIGS. 3 through 5, a test strip 76 is positioned in the lead-in area 45 at the distal end of the device body 10 and adjacent to the lancet device 30 as a user engages the lancet device 30 with a skin surface 95. In doing so, a bottom surface of a finger can be lanced as shown in FIGS. 3 and 4, or a side surface of a finger can be lanced as shown in FIG. 5. The user can then apply the blood drop from the skin surface 95 to the test strip 76 in a number of motions, each requiring a minimal travel distance and device manipulations. Specifically, the user can use the device tip to rest the lanced finger and provide a guide while rolling the blood drop to the adjacent test strip 76, the user can use a second finger to rest the lanced finger and provide a guide while rolling the blood drop to the adjacent test strip 76, the user can rotate the lanced finger about the stationary device to provide the blood drop to the adjacent test strip 76, or the user can simply move the lanced finger a short distance to provide the blood drop to the adjacent test strip 76.

In FIGS. 6 and 7, the user is shown applying the blood drop from the skin surface 95 onto the test strip 76 that is positioned in the lead-in area 45. Specifically, the user engages the lancet device 30 with a skin surface 95 (in this case, the bottom surface of the finger) by rolling the skin surface 95 over the tip of the lancet device 30. The tip of the lancet device 30 includes a substantially cylindrical depth control mechanism 32 against which the user engages the skin surface 95. Once lanced, the lancet device 30 is withdrawn slightly from the skin surface 95 to allow the formation of a blood drop on the skin surface 95. The user can then place a different part of the finger (in this case, the side surface of the finger) on the top of the tip of the lancet device 30 as a rest/support surface. In such a rested/supported position, the user can then rotate the lanced finger toward the test strip 76 to apply the blood drop from the skin surface 95 onto the test strip 76 as shown in FIGS. 6 and 7 with less effort, yet with a greater degree of control and precision. The embodiments of the present invention still further allow the user to use a second or adjacent finger as a rest or support when rotating the lanced finger to apply the blood drop onto the test strip 76.

Where a rest or support is not required or desired by the user, the user can simply move the finger the short distance between lancet device 30 and the adjacent test strip 76 to apply the blood drop onto the test strip 76 as shown in FIGS. 8 and 9. FIGS. 8 and 9 are views illustrating an exemplary manner of use of an embodiment of the present invention by moving a side-lanced finger a short distance to the test strip to provide the blood drop to the test strip.

In the above manners of use, the user can either rotate the finger against the lancet device 30 and toward the test strip 76 in a substantially continuous motion, or move the finger to apply the blood drop onto the test strip 76. For example, the embodiments of the present invention provide for a manner of use in which the finger is rotated against a stationary, or substantially stationary device. FIGS. 10 through 12 are views illustrating an exemplary manner of use of an embodiment of the present invention by rolling the finger over a stationary device and toward a test strip in a substantially continuous motion to provide the blood drop to the test strip. Specifically, in such a "strip-to-tip rotate" method, the user engages the lancet device 30 with a skin surface 95 by rolling the skin surface 95 over the tip of the lancet device 30 to produce a blood drop as shown in FIG. 10. Once lanced, the lancet device 30 is withdrawn slightly from the skin surface 95 to allow the formation of the blood drop. The user can then rotate the finger to bring the blood drop toward the adjacent test strip 76 to apply the blood drop onto the test strip 76 as shown in FIGS. 11 and 12 with less effort, yet with a greater degree of control and precision. In this manner of use, the finger is rotated about the stationary device.

Another feature of the embodiments of the present invention described above is the one-handed use of the embodiments to access the test strip vial 75 located in the enclosure 70 at the proximal end of the device body 10. In FIGS. 13 through 16, a user is shown opening and closing the test strip vial 75 with one hand. FIGS. 13 through 16 are views illustrating an exemplary manner of use of an embodiment of the present invention for using a single hand to access a test strip vial.

Accordingly, the embodiments of the present invention can include a blood glucose meter 80 with an integral lancet device 30, and an enclosure 70 provided on the device body 10 to store a test strip vial 75 that holds a number of test strips. As noted in FIGS. 1 and 2, the embodiments house the glucose test strip vial 75 in a compartment or enclosure 70 that is located at the proximal end of the device. In doing so, all of the supplies that are typically required for a test are located in the body of the device.

Most existing blood glucose meters have a separate test strip vial, and at least one existing device has the test strips mounted on a carousel for dispensing. The embodiments of the present invention described above, however, combine a blood glucose meter 80, lancet device 30, and test strip storage 70, into one device. These embodiments can include any number of variations, however, each combining a lancet device 30 and blood glucose meter 80, with provisions to store a test strip vial 75.

The embodiments of the present invention can provide any number of types of inboard, or on-device storage for a strip vial 75 in a meter-lancet device combination, and include any number of types of retention features for the test strip vial 75, such as a friction-type retention feature, a positive mechanical lock, or other similar mechanism for engaging and retaining the test strip vial 75 in the enclosure 70. However, in each embodiment and versions thereof, the test strip vial 75 and enclosure 70 are preferably constructed so that the test strip vial 75 can be operated with one hand as shown in FIGS. 13 through 16.

Figure 13:
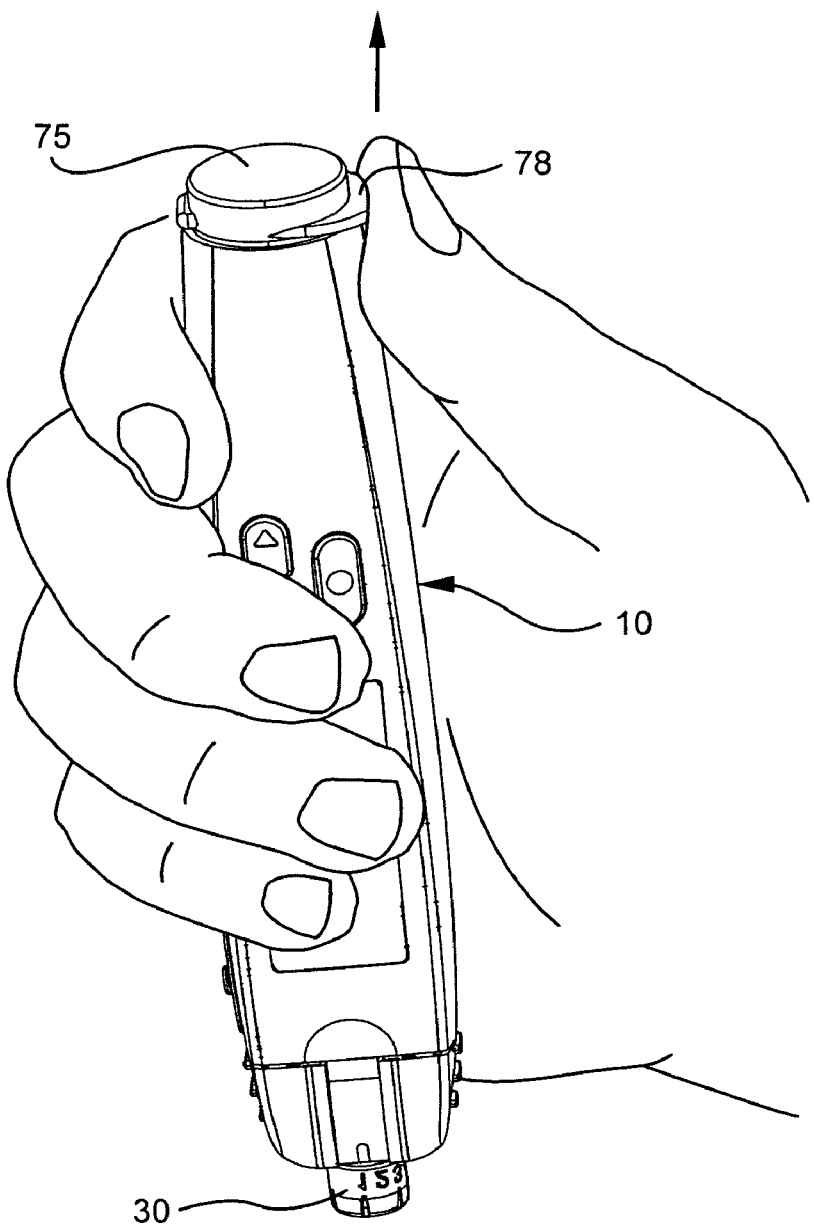
FIGS. 13 through 16 are views illustrating an exemplary manner of use of an embodiment of the present invention for using a single hand to open and close a test strip vial to access a test strip.
Figure 14:
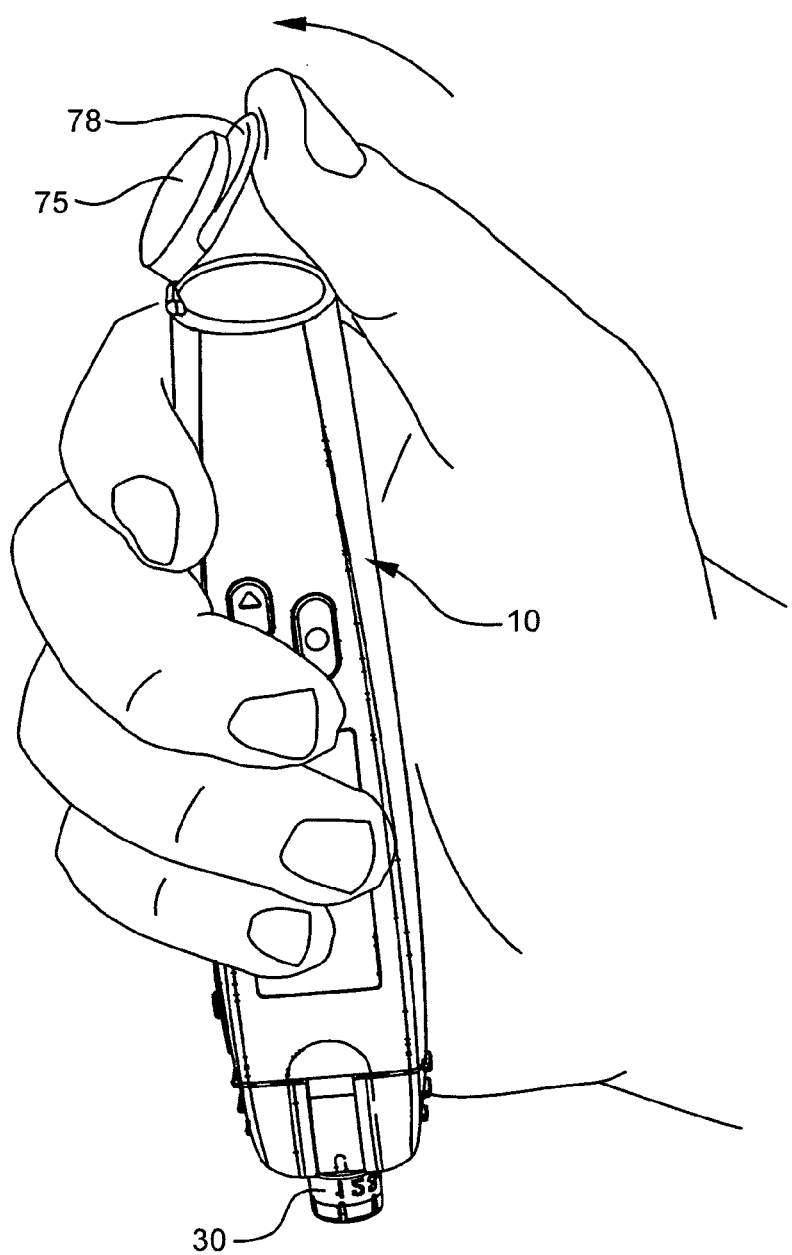
Figure 15:
Figure 16:
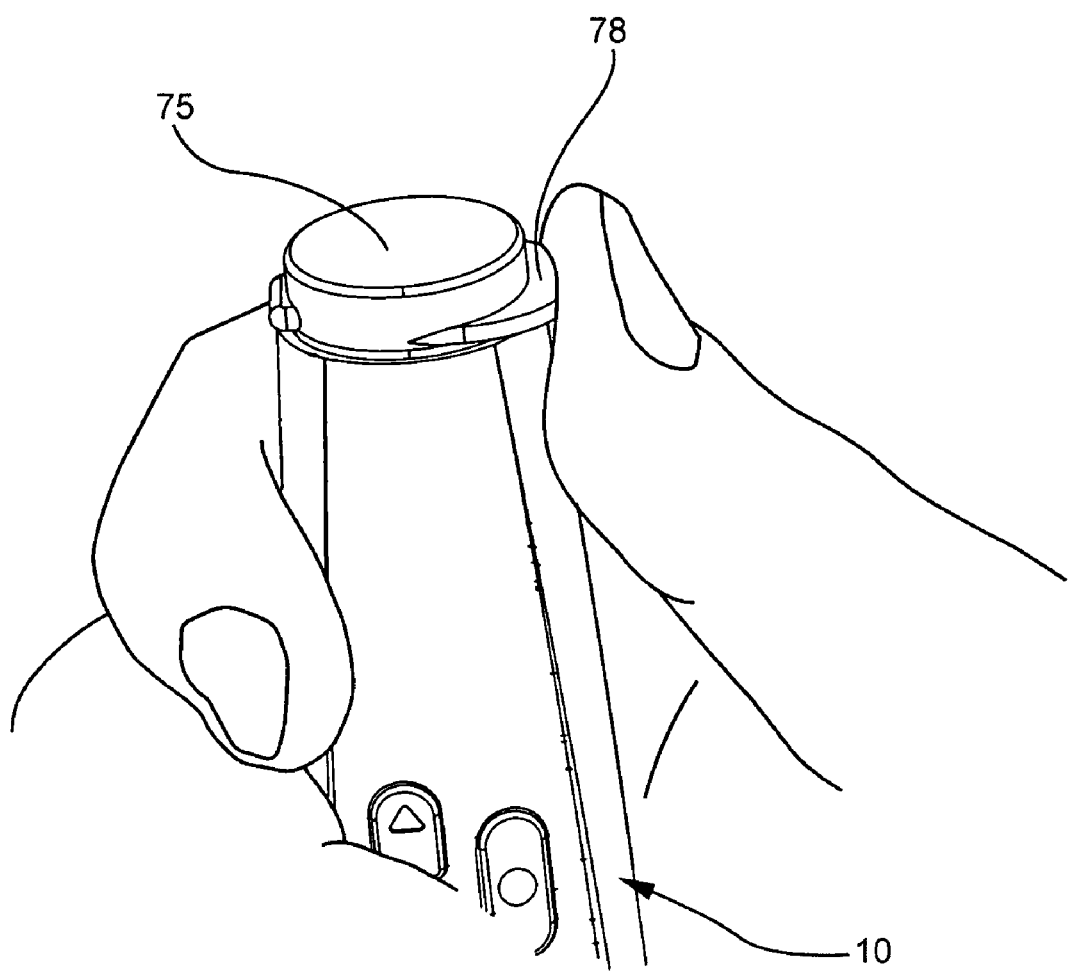

FIGS. 13 through 16 illustrate a one-handed use of an embodiment of the present invention, including a test strip vial 75 and an enclosure 70 with a combined lancet device 30 and blood glucose meter 80. In FIG. 13, a user holds the device body 10 in one hand and positions a finger at the proximal end of the device body 10. Using the finger of one hand, the user can then open the test strip vial 75 located in the enclosure 70 at the proximal end of the device body as shown in FIG. 14 to remove a test strip for use. The user can still further close the test strip vial 75 located at the proximal end of the device body as shown in FIG. 15. The opening and closing operations of the test vial 75 can be further achieved through the use of an extended test vial cap 78 as shown in greater detail in FIG. 16.

Although only a few exemplary embodiments of the apparatus and methods of the present invention have been described in detail above, those skilled in the art will readily appreciate that many modifications are possible in the exemplary embodiments without materially departing from the novel teachings and advantages of the present invention.

Accordingly, all such modifications are intended to be included within the scope of the present invention as defined in the appended claims and equivalents thereof.

What is claimed is:

1. A blood glucose meter device for single handed use, comprising:
    a body having first and second ends and an upper surface extending between said first and second ends;
    a lancet device disposed at said first end of said body;
    a depth control mechanism configured for contacting the skin to be lanced and located at said first end of said body, wherein said depth control mechanism is rotatable for setting a lancet skin penetration depth;
    a test strip port, opening to said upper surface proximate to said first end of said body for positioning a test strip along an exterior surface of said body, adjacent to said lancet device; and
    a display disposed on said upper surface between said test strip port and said second end of said body, wherein said display and said test strip port are disposed at adjacent positions upon said upper surface for simultaneous viewing of said display and said test strip.

2. A blood glucose meter device as claimed in claim 1, wherein said body further comprises a test strip lead-in area extending between said test strip port and said lancet device.

3. A blood glucose meter device as claimed in claim 1, wherein said body further comprises:
    at least one operator control for data entry and review through said display.

4. A blood glucose meter device as claimed in claim 1, further comprising a data connector disposed on said body for communication access.

5. A blood glucose meter as claimed in claim 4, wherein said communication access comprises at least one of a data upload operation and a data download operation.

6. A blood glucose meter device as claimed in claim 1, wherein said lancet device comprises:
    a trigger button disposed on said body for activating said lancet device; and
    an arming slide disposed on said body for arming said lancet device.

7. A blood glucose meter device as claimed in claim 6, wherein said lancet device further comprises a surface for supporting said skin surface when rolled toward said adjacent test strip.

8. A blood glucose meter device as claimed in claim 1, wherein said body further comprises a detachable cover at said first end of said body for providing access to said lancet device for loading and unloading of lancets.

* * * * *